(12) United States Patent
Tanigawara et al.

(10) Patent No.: US 9,089,540 B2
(45) Date of Patent: Jul. 28, 2015

(54) METHOD FOR DETERMINATION OF SENSITIVITY TO ANTI-CANCER AGENT

(75) Inventors: Yusuke Tanigawara, Tokyo (JP); Sayo Suzuki, Tokyo (JP); Shinji Sugimoto, Tokyo (JP)

(73) Assignees: KEIO UNIVERSITY, Tokyo (JP); KABUSHIKI KAISHA YAKULT HONSHA, Tokyo (JP)

( * ) Notice: Subject to any disclaimer, the term of this patent is extended or adjusted under 35 U.S.C. 154(b) by 447 days.

(21) Appl. No.: 12/865,726

(22) PCT Filed: Jan. 30, 2009

(86) PCT No.: PCT/JP2009/000374
§ 371 (c)(1),
(2), (4) Date: Aug. 1, 2010

(87) PCT Pub. No.: WO2009/096196
PCT Pub. Date: Aug. 6, 2009

(65) Prior Publication Data
US 2010/0323034 A1   Dec. 23, 2010

(30) Foreign Application Priority Data

Jan. 31, 2008 (JP) ................................ 2008-021124
Sep. 1, 2008 (JP) ................................ 2008-223384

(51) Int. Cl.
| | | |
|---|---|---|
| *A61K 31/282* | (2006.01) | |
| *G01N 33/574* | (2006.01) | |
| *A61K 45/06* | (2006.01) | |
| *G01N 33/50* | (2006.01) | |

(52) U.S. Cl.
CPC .............. *A61K 31/282* (2013.01); *A61K 45/06* (2013.01); *G01N 33/5011* (2013.01); *G01N 33/57484* (2013.01); *G01N 2333/4727* (2013.01); *G01N 2800/52* (2013.01)

(58) Field of Classification Search
None
See application file for complete search history.

(56) References Cited

U.S. PATENT DOCUMENTS

| 7,700,280 | B2 * | 4/2010 | Al-Murrani | ................... 435/6.12 |
|---|---|---|---|---|
| 2004/0076955 | A1 * | 4/2004 | Mack et al. | ....................... 435/6 |
| 2005/0176669 | A1 | 8/2005 | Al-Murrani | |
| 2007/0054271 | A1 | 3/2007 | Polyak et al. | |
| 2009/0258795 | A1 * | 10/2009 | Cowens et al. | .................. 506/16 |
| 2010/0216131 | A1 * | 8/2010 | Luthra et al. | ....................... 435/6 |
| 2010/0233680 | A1 * | 9/2010 | Taylor et al. | ....................... 435/6 |

FOREIGN PATENT DOCUMENTS

| CN | 1922332 A | 2/2007 | |
|---|---|---|---|
| CN | 101011351 A | 8/2007 | |
| CN | 101040843 A | 9/2007 | |
| JP | 2007 517058 | 6/2007 | |
| WO | WO 2005/066371 A2 | 7/2005 | |
| WO | WO 2005/121786 | 12/2005 | |
| WO | 2007 058968 | 5/2007 | |
| WO | WO 2007/134779 | * 11/2007 | ............. G01N 33/53 |

OTHER PUBLICATIONS

U.S. Appl. No. 13/505,175, filed Apr. 30, 2012, Tanigawara, et al.
Shirota, Yoshinori et al., "ERCCI and Thymidylate Synthase mRNA Levels Predict Survival for Colorectal Cancer Patients Receiving Combination Oxaliplatin and Fluorouracil Chemotheraphy", Journal of Clinical Oncology, vol. 19, No. 23, pp. 4298-4304, (Dec. 1, 2001).
Stoehlmacher, J. et al., "A multivariate analysis of genomic polymorphisms: prediction of clinical outcome to 5-FU/oxaliplatin combination chemotheraphy in refractory colorectal cancer", British Journal of Cancer, vol. 91, No. 2, pp. 344-354, (2004).
Park, J. David et al., "A Xeroderma Pigmentosum Group D Gene Polymorphism Predicts Clinical Outcome to Platinum-based Chemotheraphy in Patients with Advanced Colorectal Cancer", Cancer Research, vol. 61, pp. 8654-8658, (Dec. 15, 2001).
Stoehlmacher, Jan. et al., "A Polymorphism of the XRCC1 Gene Predicts for Response to Platinum Based Treatment in Advanced Colorectal Cancer", Anticancer Research, vol. 21, pp. 3075-3080, (2001).
Fink, Daniel et al., "The Role of DNA Mismatch Repair in Platinum Drug Resistance", Cancer Research, vol. 56, pp. 4881-4886, (Nov. 1, 1996).
Stoehlmacher, Jan. et al., "Association Between Glutathione S-Transferase P1, T1, and M1 Genetic Polymorphism and Survival of Patients With Metastatic Colorectal Cancer", Journal of the National Cancer Institute, vol. 94, No. 12, pp. 936-942, (Jun. 19, 2002).
Zhang, Shuzhong et al., "Organic Cation Transporters are Deterninants of Oxaliplatin Cytotoxicity", Cancer Res., vol. 66, No. 17, pp. 8847-8857, (Sep. 1, 2006).
Samimi, Goli et al., "Modulation of the Cellular Pharmacology of Cisplatin and its Analogs by the Copper Exporters ATP7A and ATP7B", Molecular Pharmacology, vol. 66, No. 1, pp. 25-32, (2004).

(Continued)

*Primary Examiner* — Mark Halvorson
(74) *Attorney, Agent, or Firm* — Oblon, McClelland, Maier & Neustadt, L.L.P.

(57) ABSTRACT

Provided are an marker for determining sensitivity to an anti-cancer agent capable of distinguishing a therapeutic response of an individual patient and a novel means for a cancer therapy using the marker. The marker for determining sensitivity to an anticancer agent contains a calcium-binding protein S100A7, S100A8, or S100A10.

17 Claims, 13 Drawing Sheets

(56) References Cited

OTHER PUBLICATIONS

Samimi, Goli et al., "Increased Expression of the Copper Efflux Transporter ATP7A Mediates Resistance to Cisplatin, Carboplatin, and Oxalipatin in Ovarian Cancer Cells", Clinical Cancer Research, vol. 10, pp. 4661-4669, (Jul. 15, 2004).

Ruzzo, Annamaria et al., "Pharmacogenetic Profiling in Patients With Advanced Colorectal Cancer Treated With First-Line FOLFOX-4 Chemotheraphy", Journal of Clinical Oncology, vol. 25, No. 10, pp. 1247-1254, (Apr. 1, 2007).

Nadal, Cristina et al., "FAS/FAS Ligand Ratio: A Marker of Oxaliplatin-Based Intrinsic and Acquired Resistance in Advanced Colorectal Cancer", Clin Cancer Res., vol. 11, No. 13, pp. 4770-4774, (Jul. 1, 2005).

Griffiths, J. Gareth et al., "Expression of Kinase-defective Mutants of c-Src in Human Metastatic Colon Cancer Cells Decreases Bcl-$x_L$ and Increases Oxaliplatin- and Fas-induced Apoptosis", The Journal of Biological Chemistry, vol. 279, No. 44, pp. 46113-46121, (Oct. 29, 2004).

Office Action issued Sep. 20, 2011, in Chinese Patent Application No. 200980103933.0 with English translation.

U.S. Appl. No. 13/504,985, filed Apr. 30, 2012, Tanigawara, et al.

U.S. Appl. No. 13/505,143, filed Apr. 30, 2012, Tanigawara, et al.

Ukrainian Office Action issued Apr. 10, 2012, in Ukrain Patent Application No. 201010512 (with English translation).

Roland Lehmann, et al., "Detection and Identification of Protein Interactions of S100 Proteins by ProteinChip Technology", Journal of proteome research, vol. 4, No. 5, 2005, pp. 1717-1721.

New Zealand Examination Report issued Oct. 10, 2011, in New Zealand Patent Application No. 586972.

"S100 calcium-binding protein A7 [Homo sapiens]", NCBI Accession No. NP_002954.2, Mar. 24, 1999, 4 pages.

U.S. Appl. No. 14/007,145, filed Sep. 24, 2013, Tanigawara, et al.

Russian Office Action in corresponding Patent Application No. 2010136309 dated May 14, 2013.

A. Hermani, et al., "Calcium-Binding Proteins S100A8 and S100A9 as Novel Diagnostic Markers in Human Prostate Cancer", Clinical Cancer Research: An official journal of the American Association for Cancer Research, Jul. 15, 2005, vol. 11, No. 14, pp. 5146-5152.

European Search Report in corresponding Patent No. 09706388.7 dated May 17, 2013.

R. Kennedy, et al., "BRCA1 and c-Myc Associate to Transcriptionally Repress Psoriasin, a DNA Damage-Inducible Gene", Cancer Research, Nov. 2005, vol. 65, No. 22, pp. 10265-10272, XP-002696449.

European Office Action issued Aug. 11, 2014 in Patent Application No. 09 706 388.7.

Bethany L. Niell et al., "BRCA1 and BRCA2 Founder Mutations and the Risk of Colorectal Cancer", Journal of the National Cancer Institute, vol. 96, No. 1, XP-055123019, Jan. 7, 2004, pp. 15-21.

\* cited by examiner

METHOD FOR DETERMINATION OF SENSITIVITY TO ANTI-CANCER AGENT

TECHNICAL FIELD

The present invention relates to a marker for determining sensitivity to an anticancer agent which is used to determine whether or not a cancer in a subject patient has a therapeutic response to an anticancer agent to be used, and to an application thereof.

BACKGROUND ART

There are various kinds of anticancer agents such as an alkylating agent, a platinum agent, an antimetabolite, an antitumor antibiotic, and an antitumor plant alkaloid. In addition, those anticancer agents exhibit the effects in some cases and exhibit no effect in other cases, which depends on the kind of cancer. However, it is known that, even if the cancer is a kind in which an anticancer agent is confirmed to be effective, the anticancer agent exhibits the effect in some cases and exhibits no effect in other cases, leading to interindividual differences. Whether an anticancer agent exhibits the effect on the cancer of an individual patient or not is designated to as sensitivity to the anticancer agent.

Oxaliplatin, i.e. (SP-4-2)-[(1R,2R)-cyclohexane-1, 2-diamine-κN,κN'][ethanedioato (2-)-κ$O^1$,κ$O^2$]platinum (IUPAC), is a third-generation platinum-based complex anticancer agent. The action mechanism thereof is thought to be, like cisplatin (CDDP) and carboplatin (CBCDA) that are preceding drugs, based on DNA synthesis inhibition and/or protein synthesis inhibition by formation of a cross-link with a DNA base. The oxaliplatin (L-OHP) exhibits an antitumor effect on colorectal cancer, in which CDDP and CBCDA are ineffective, and shows different spectrum of antitumor activity from that of a conventional platinum-based complex anticancer agent. In America, oxaliplatin for use in combination with fluorouracil (5-FU) and levofolinate (LV) was approved as a first line therapy for metastatic colorectal cancer in January 2004. In Japan, in April 2005, the oxaliplatin was listed on National Health Insurance (NHI) price listing in the case of combination use thereof with an infusional fluorouracil and levofolinate (FOLFOX4 regimen) for advanced/recurrent colorectal cancer not amenable to curative surgical resection. In the treatment for advanced/recurrent colorectal cancer, while the survival with a 5-FU/LV regimen which had been given until the early 1990s was in the range of 10 to 12 months, the survival with the FOLFOX regimen combined with oxaliplatin reaches about twice the period (19.5 months). In addition, in a study with stage II/III cases, there is reported the efficacy of the FOLFOX regimen when compared with the 5-FU/LV regimen in a postoperative adjuvant chemotherapy.

Accordingly, though the oxaliplatin has not yet been approved, oxaliplatin is expected to be supplemental approval for use of patient treatment with colorectal cancer in postoperative adjuvant chemotherapy and to be effective in the patients.

Nevertheless, an objective response rate of the FOLFOX regimen against advanced/recurrent colorectal cancer is about 50%. In other words, it is suggested that the half of the patients who have received the FOLFOX regimen do not achieve the effect. In addition, the use of the oxaliplatin causes a peripheral neuropathy at high frequency in addition to neutropenia, which is not a fatal adverse event but is a factor causing a difficulty in continuing the therapy. Therefore, if a patient who is expected to achieve the response (responder) and a patient who is not expected to achieve the response (non-responder) can be predicted or diagnosed before starting the therapy, highly effective and safe chemotherapy can be realized. Further, in general, the treatment schedule of cancer chemotherapy extends for a long period. Therefore, monitoring sensitivity to an anticancer agent chronologically during the therapy enables the determination on whether the therapy must be continued or not, leads to reduction in burden of the patient and adverse events, and may also be effective from the viewpoint of the medical economy. The establishment of a biomarker for predicting a therapeutic response is urged for "personalized medicine" in which the therapeutic response of individual patients is predicted and an appropriate therapy is selected.

As factors related with the therapeutic response to the oxaliplatin, the following may be mainly involved:

(1) enhancement of the ability of excision repairing damaged DNA by the oxaliplatin;

(2) inactivation (detoxication) of the oxaliplatin (activated form) in cells; and (3) reduction in accumulation amount of the oxaliplatin in cells.

There are conducted clinical studies on the therapeutic response in a therapy using oxaliplatin and 5-FU in combination for colorectal cancer patients, and clinical studies related with the above items (1) to (3) as predictive factors for prognosis.

Regarding the item (1), there is reported that excision repair cross-complementing group 1 (ERCC1) gene expression amount in tumor is a prognostic factor, the ERCC1 playing an important role in a nucleotide excision repair (NER) (Non-patent Document 1). There is reported that a patient having C/C homozygote of C118T, which is one of single nucleotide polymorphisms (SNPs) of ERCC1, shows more favorable survival rate than that of a patient having at least one or more T alleles (Non-patent Document 2). The genetic polymorphism which causes an amino acid mutation of Lys751Gln in Xeroderma pigmentosum D (XPD, also known as ERCC2), is reported to be involved in tumor reduction rate or the survival (Non-patent Documents 2 and 3). In the base excision repair (BER), there is reported the relationship between the tumor reduction effect and the genetic polymorphism which causes the amino acid mutation of Arg399Gln in X-ray repair cross-complementing group 1 (XRCC1) and, the XRCC1 encoding the protein which may be involved in the effective repair of the breakage of a DNA single strand formed by exposure to an alkylating agent or the like (Non-patent Document 4). However, by the analysis targeting the same patients afterwards, the genetic polymorphism is reported not to influence clinical prognosis (Non-patent Document 2). The DNA mismatch repair (MMR) may also be related with the reduction in sensitivity to cisplatin. However, in a study in vitro, MMR is reported not to be involved in the repair of DNA damaged by oxaliplatin (Non-patent Document 5).

Regarding the item (2), glutathione-S-transferase (GST) is one of enzymes which are responsible for the second phase reaction of the detoxication and metabolism, and inactivates a drug by catalyzing the formation of a conjugation of a platinum-DNA adduct and glutathione. Among GST subtypes, GSTP1 has a high expression level in colorectal cancer. In addition, the genetic polymorphism of the GSTP1, which causes the amino acid mutation of Ile105Val, is reported to be related with the survival (median survival: Ile/Ile, 7.9 months; Ile/Val, 13.3 months; and Val/Val, 24.9 months) (Non-patent Document 6).

Regarding the item (3), in a study using cultured cells, it is reported organic cation transporters (OCTs) are related with the transport of oxaliplatin into the cells and the sensitivity (Non-patent Document 7). In addition, there is reported a relationship between a transporter involving the transport of a copper or a heavy metal, such as ATP7A or ATP7B, and the sensitivity (Non-patent Documents 8 and 9). However, there is no clinical study on the relationship between the expression of those transporters and the therapeutic response to oxaliplatin.

In recent clinical study for advanced colorectal cancer received FOLFOX regimen, it is reported that the genetic polymorphism of ERCC1 (Asn118Asn) and the genetic polymorphism of XPD (Lys751Gln) are independently related with the progression-free survival (PFS). However, there is not found the relationship between the genetic polymorphism of GSTP1 (Ile105Val) and PFS, and it is recognized that the genetic polymorphism tends to have a relationship with oxaliplatin-induced neurotoxicity (Non-patent Document 10).

In studies in vitro, there are many reports on a resistance-related factor of the cisplatin which is a platinum-based complex, preceding drug. There is also reported the relationship between oxaliplatin and apoptosis-related factors such as FAS/FASL and Bcl-xL (Non-patent Documents 11 and 12). However, depending on the kind of cancer, the oxaliplatin exhibits different therapeutic response from the cisplatin. In addition, the cellular response of a cancer cell to a platinum DNA adduct responsible for a cytotoxic activity of oxaliplatin is hardly clarified. A biomarker capable of clearly predicting a therapeutic response to a chemotherapy using the oxaliplatin has been yet to be established.

RELATED ART DOCUMENTS

[Non-patent Document 1] J. Clin. Oncol. 19, 4298-4304 (2001)
[Non-patent Document 2] Br. J. Cancer 91, 344-354 (2004)
[Non-patent Document 3] Cancer Res 61, 8654-8658 (2001)
[Non-patent Document 4] Anticancer Res. 21, 3075-3079 (2001)
[Non-patent Document 5] Cancer Res. 56, 4881-4886 (1996)
[Non-patent Document 6] J. Natl. Cancer Inst. 94, 936-942 (2002)
[Non-patent Document 7] Cancer Res. 66, 8847-8857 (2006)
[Non-patent Document 8] Mol. Pharmacol. 66, 25-32 (2004)
[Non-patent Document 9] Clin. Cancer Res. 10, 4661-4669 (2004)
[Non-patent Document 10] J. Clin. Oncol. 25, 1247-1254 (2007)
[Non-patent Document 11] Clin. Cancer Res. 11, 4770-4774 (2005)
[Non-patent Document 12] J. Biol. Chem. 279, 46113-46121 (2004)

DISCLOSURE OF THE INVENTION

Problems to be solved by the Invention

An object of the present invention is to provide an marker for determining sensitivity to an anticancer agent capable of determining therapeutic response of individual patients and to provide a novel means for a cancer therapy using the marker.

Means for solving the Problems

The inventors of the present invention cultured human cancer cell lines and searched an marker for determining sensitivity to an anticancer agent from their intracellular proteins by using a surface-enhanced laser desorption/ionization time-of-flight mass spectrometer (SELDI-TOF MS). As a result, the inventors found proteins whose expression levels increase with reduction in sensitivity to an anticancer agent, and the proteins were found to be three kinds of proteins detected as peaks at m/z of 10,800 to 11,400 with the mass spectrometer. Then, the inventors further studied on the proteins, with the result that those proteins were found to be calcium-binding proteins, i.e. S100A7, S100A8, and S100A10, which were known to be members of S100 protein family having a calcium-binding EF-hand motif.

The inventors further studied based on the finding, and have found that: whether the cancer of a cancer patient has sensitivity to an anticancer agent or not can be determined by measuring the concentration of S100A7, S100A8, or S100A10 in a biological sample derived from the cancer patient; the use of the expression inhibition of the protein as an index enables the screening of an agent for enhancing sensitivity to an anticancer agent (hereinafter referred to as "anticancer agent sensitivity-enhancing agent"); and the therapeutic effect of the anticancer agent is remarkably improved by using the anticancer agent sensitivity-enhancing agent and the anticancer agent as a target of the sensitivity enhancement in combination. Thus, the present invention has been completed.

That is, the present invention provides a marker for determining sensitivity to an anticancer agent containing a calcium-binding protein S100A7, S100A8, or S100A10.

The present invention also provides a method of determining sensitivity to an anticancer agent, including measuring a concentration of the S100A7, S100A8, or S100A10 in a specimen.

The present invention also provides a kit for conducting the method of determining sensitivity to an anticancer agent, containing a protocol for measuring a concentration of the S100A7, S100A8, or S100A10 in a specimen.

The present invention also provides a method of screening an anticancer agent sensitivity-enhancing agent, including using an expression inhibition of the S100A7, S100A8, or S100A10 as an index.

The present invention also provides an anticancer agent sensitivity-enhancing agent, which is obtained by the above screening method.

The present invention also provides a composition for a cancer therapy containing a combination of the above anticancer agent sensitivity-enhancing agent and an anticancer agent as a target of sensitivity enhancement.

The present invention also provides use of the combination of the above anticancer agent sensitivity-enhancing agent and an anticancer agent as a target of sensitivity enhancement for producing a therapeutic drug for cancer.

The present invention also provides a method of treating cancer, including administering the above anticancer agent sensitivity-enhancing agent and an anticancer agent as a target of sensitivity enhancement.

Effects of the invention

If the marker for determining sensitivity to an anticancer agent of the present invention is used, sensitivity to an anticancer agent of an individual patient can be appropriately determined before the starting of a therapy, with the result that an anticancer agent having high therapeutic effect can be selected. Further, the use of an anticancer agent having no effect can be avoided, whereby unnecessary adverse event can be avoided. In addition, the schedule of a therapy using an anticancer agent extends for a long period, and hence the sensitivity of the cancer to the anticancer agent can be evaluated chronologically by determining sensitivity to the anticancer agent in each therapeutic cycle even during the therapy, and thus, whether the therapy must be continued or not can be determined. As a result, the progression of the cancer and the enhancement of adverse events, which accompany continuous administration of the anticancer agent having no therapeutic effect, can be prevented, resulting in the reduction in burden of the patient and the cut of medical expenses.

Further, if the marker is used, an anticancer agent sensitivity-enhancing agent can be screened. A cancer therapeutic effect is remarkably improved by using the anticancer agent sensitivity-enhancing agent and the anticancer agent as a target thereof in combination.

BEST MODE FOR CARRYING OUT THE INVENTION

Figure 1:
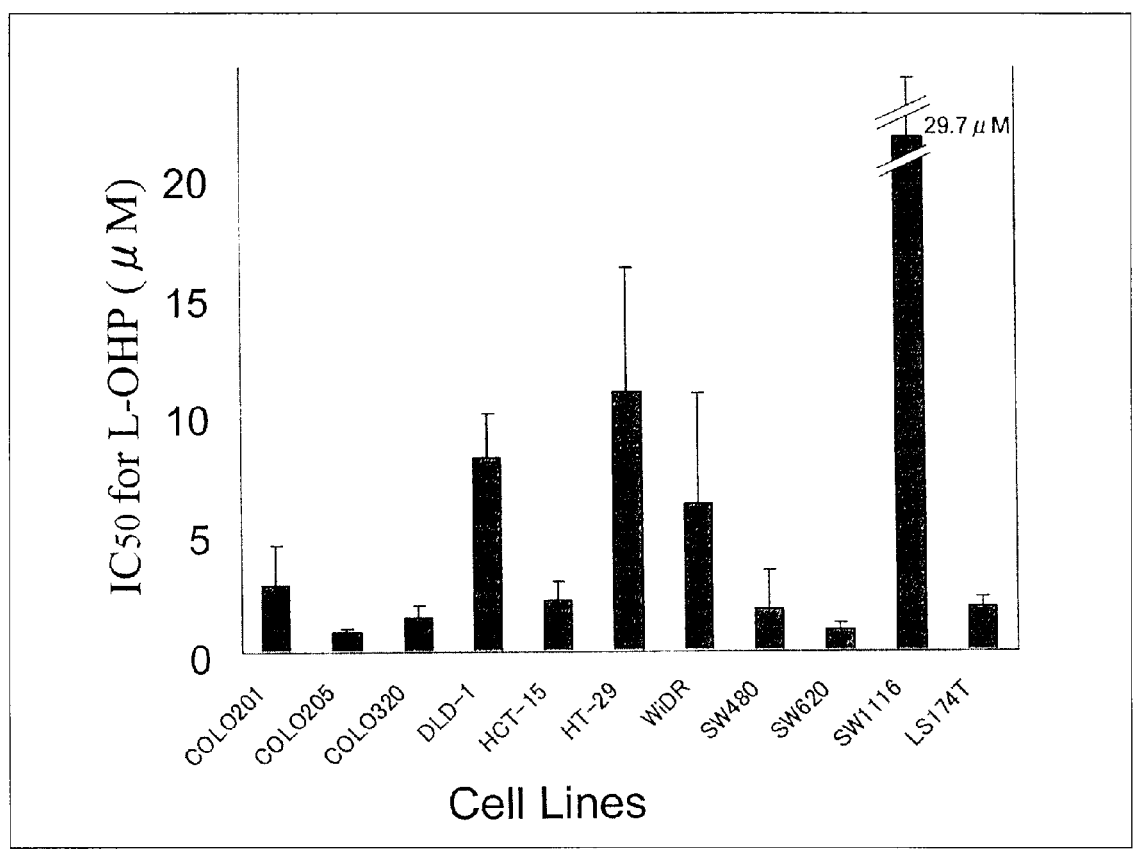
FIG. 1 is a graph illustrating sensitivity to oxaliplatin (L-OHP) in each cancer cell line.

The marker for determining sensitivity to an anticancer agent of the present invention contains, S100A7, S100A8, or S100A10. Those proteins are detected as peaks at m/z of 10,800 to 10,900 (S100A8), 11,000 to 11,100 (S100A10), and 11,300 to 11,400 (S100A7) by surface-enhanced laser desorption/ionization time-of-flight mass spectrometer (SELDI-TOF MS).

As a result of a study of intracellular protein expression in cultured cancer cells by using SELDI-TOF MS, as described in Examples below, those proteins S100A7, S100A8, and S100A10 (hereinafter, each also referred to as protein A) were found to have a significant correlation with sensitivity to oxaliplatin ($IC_{50}$ value), sensitivity to cisplatin ($IC_{50}$ value), or sensitivity to irinotecan or SN-38 ($IC_{50}$ value). That is, the expression level of the protein A was low in cancer cells having high sensitivity to oxaliplatin, cisplatin, irinotecan, or SN-38 whereas the expression level of the protein A was high in cancer cells having low sensitivity to oxaliplatin, cisplatin, irinotecan, or SN-38. Accordingly, the protein A is effective as a marker for determining sensitivity to an anticancer agent, specifically as a marker for determining sensitivity to a platinum-based complex anticancer agent or a plant alkaloid-derived anticancer agent, and more specifically as a marker for determining sensitivity to oxaliplatin, cisplatin, irinotecan, SN-38, or salts thereof.

Here, because it is known that S100A8 and S100A7 possibly bind to S100A10 (Journal of Proteome Research 2005; 4: 1717-1721), those proteins may have some interactions to sensitivity to an anticancer agent. In addition, those bound forms may be also used as a marker for determining sensitivity to an anticancer agent. Further, it is known that the dimer of S100A10 itself and the dimer of annexin A2 (Annexin-2, Annexin II, Lipocortin II, Calpactin I heavy chain, Chromobindin-8, p36, Protein I, Placental anticoagulant protein IV, PAP-IV) form a heterotetramer, and hence the annexin A2 may also be used as a marker for determining sensitivity to an anticancer agent as well as S100A10.

The anticancer agent as a target of the marker for determining sensitivity to an anticancer agent of the present invention is not particularly limited. Examples thereof include oxaliplatin, cyclophosphamide, ifosfamide, thiotepa, melphalan, busulfan, nimustine, ranimustine, dacarbazine, procarbazine, temozolomide, cisplatin, carboplatin, nedaplatin, methotrexate, pemetrexed, fluorouracil, tegaful/uracil, doxifluridine, tegaful/gimeracil/oteracil, capecitabine, cytarabine, enocitabine, gemcitabine, 6-mercaptopurine, fuludarabin, pentostatin, cladribine, hydroxyurea, doxorubicin, epirubicin, daunorubicin, idarubicine, pirarubicin, mitoxantrone, amurubicin, actinomycin D, bleomycine, pepleomycin, mytomycin C, aclarubicin, zinostatin, vincristine, vindesine, vinblastine, vinorelbine, paclitaxel, docetaxel, irinotecan, irinotecan active metabolite (SN-38), nogitecan (topotecan), etoposide, prednisolone, dexamethasone, tamoxifen, toremifene, medroxyprogesterone, anastrozole, exemestane, letrozole, rituximab, imatinib, gefitinib, gemtuzumab ozogamicin, bortezomib, erlotinib, cetuximab, bevacizumab, sunitinib, sorafenib, dasatinib, panitumumab, asparaginase, tretinoin, arsenic trioxide, salts thereof, and active metabolites thereof. Of those, platinum-based complex anticancer agents and plant alkaloid-derived anticancer agents are preferred and oxaliplatin, cisplatin, irinotecan, SN-38, or a salt thereof is particularly preferred.

In order to determine sensitivity to an anticancer agent by using the marker for determining sensitivity to an anticancer agent of the present invention, the concentration of the protein A in a specimen may be measured. Here, examples of the specimen include a biological sample derived from a subject carrying cancer (cancer patient), such as blood, serum, plasma, a biopsy specimen of a cancer tissue, a preparation obtained by cancer extirpation, stool, urine, ascitic fluid, pleural fluid, cerebrospinal fluid, or expectoration. The serum is particularly preferred.

In addition, examples of the target cancer in the present invention include lip, oral, and pharyngeal cancers typified by pharyngeal cancers; gastrointestinal cancers typified by esophageal cancer, gastric cancer, and colorectal cancer; respiratory and intrathoracic organ cancers typified by lung cancer; bone and articular cartilage cancers; malignant melanoma, squamous cell carcinoma of skin and other cancer of skin; mesothelial and soft tissue cancers typified by mesothelioma; female genital cancers typified by breast cancer, uterine cancer, and ovarian cancer; male genital cancers typified by prostate cancer; urinary tract cancers typified by bladder cancer; eye, brain, and central nervous system cancers typified by brain tumor; thyroid cancer and other endocrine cancers; lymphoid tissue, hematopoietic tissue, and related tissue cancers typified by non-Hodgkin's lymphoma, lymphoid leukemia; and metastatic cancers, primary focuses of which are those cancers. The present invention can particularly suitably be used for gastric cancer and colorectal cancer.

The concentration of the protein A can be measured by measuring means such as SELDI-TOF MS, an immunological measurement method, or the like.

The measurement by the SELDI-TOF MS can be performed by the method described in Examples below. In addition, as the immunological measurement method, an immunological measurement method using an anti-protein A antibody is preferred. The anti-protein A antibody to be used may be a monoclonal antibody or a polyclonal antibody. More specifically, a radioimmunoassay, an enzyme immunoassay, a fluorescent immunoassay, a luminescence immunoassay, immunoprecipitation, immunonephelometry, western blotting, immunostaining, and immunodiffusion are exemplified. The western blotting or the enzyme immunoassay is preferred and the western blotting or an enzyme-linked immunosorbent assay (ELISA) (for example, sandwich ELISA) is particularly preferred.

In order to determine the sensitivity to a target anticancer agent, the concentration of the protein A in a biological sample derived from a cancer patient before administration of the anticancer agent is measured. In the case where the concentration of the protein A is determined to be higher than the predetermined standard concentration, the cancer can be determined not to have sensitivity to the target anticancer agent. In addition, the concentration of the protein A in a biological sample derived from a cancer patient who is receiving an anticancer agent is measured and monitored in each therapy cycle, whereby the sensitivity of the cancer to the target anticancer agent can be evaluated chronologically. Thus, the protein A can be used as a marker for determining whether the therapy must be continued or not.

In the case where the cancer does not have sensitivity to the target anticancer agent, the drug effect cannot be expected and only the adverse event by the anticancer agent may be developed. Therefore, the marker for determining sensitivity to an anticancer agent of the present invention can be used as a marker for avoiding the expression of unnecessary adverse event or avoiding the advance of the cancer and enhancement of the adverse event caused by a continued ineffective therapy.

In addition, in the case where the concentration of the protein A is determined to be lower than the predetermined standard concentration, the cancer can be determined to have sensitivity to the target anticancer agent. Accordingly, the protein A can also be used as a marker for positively selecting patients who can be expected to have the therapeutic effect.

Further, when the protein A is used as an index, an anticancer agent can be screened. That is, if, in vitro, after various kinds of cancer cell lines each having the protein A at a high concentration are exposed to a substance, the substance exhibits an effect of killing the cells, the substance is anticancer agent effective also against cancer having low sensitivity to a platinum-based complex anticancer agent such as oxaliplatin, a plant alkaloid-derived anticancer agent such as irinotecan, or the above conventional anticancer agents. In addition, if, in vivo, after a substance is administered to a cancer-bearing animal whose biological sample has the protein A at a high concentration, an tumor reduction effect is developed, the substance is an anticancer agent effective also against cancer having low sensitivity to a platinum-based complex anticancer agent such as oxaliplatin, a plant alkaloid-derived anticancer agent such as irinotecan, or the above conventional anticancer agents. Through the screening using the protein A as an index and using various kinds of cancer cell lines each having the protein A at a high concentration or a cancer-bearing animal whose biological sample has the protein A at a high concentration, it can be determined whether the substance is effective as an anticancer agent exhibiting an antitumor effect against cancers having low sensitivity to a platinum-based complex anticancer agent such as oxaliplatin, a plant alkaloid-derived anticancer agent such as irinotecan, or the above conventional anticancer agents. A great effect can also be expected from the viewpoint of the reduction in the labor and cost accompanying the development of an anticancer agent.

It is preferred to use a kit containing a protocol for measuring the concentration of the protein A in a specimen in order to conduct a method of determining sensitivity to an anticancer agent of the present invention. The kit contains a reagent for measuring the concentration of the protein A, directions for use of the measurement reagent, a standard for determining the presence or absence of sensitivity to an anticancer agent, and the like. The standard refers to the standard concentration of the protein A, a concentration which is determined to be high or low, a factor influencing the measurement result, the degree of the influence, and the like. Those concentrations can be set for each target anticancer agent. By using the standard, the determination can be conducted as described above.

If the expression inhibition of the protein A is used as an index, the screening of an anticancer agent sensitivity-enhancing agent can be conducted. That is, in vitro or in vivo, a substance inhibiting the expression of the protein A enhances sensitivity to an anticancer agent sensitivity. For example, in vitro, a substance decreasing the concentration of the protein A in the absence or presence of an anticancer agent in various kinds of cancer cell lines is a substance enhancing the sensitivity to the anticancer agent (anticancer agent sensitivity-enhancing agent). In addition, in vivo, in a cancer-bearing animal, a substance enhancing the decrease in the concentration of the protein A before or during the administration of an anticancer agent is a substance enhancing the sensitivity to the anticancer agent (anticancer agent sensitivity-enhancing agent).

If the thus obtained anticancer agent sensitivity-enhancing agent and an anticancer agent as a target of the sensitivity enhancement are used in combination, the therapeutic effect of the anticancer agent is remarkably improved. The form of the combination of an anticancer agent sensitivity-enhancing agent and an anticancer agent as a target of the sensitivity enhancement may be a composition including the components of both agents, or may be a combination of separate preparations. In addition, those components may be administrated through different routes.

The target anticancer agent used herein is the same as described above and oxaliplatin, cyclophosphamide, ifosfamide, thiotepa, melphalan, busulfan, nimustine, ranimustine, dacarbazine, procarbazine, temozolomide, cisplatin, carboplatin, nedaplatin, methotrexate, pemetrexed, fluorouracil, tegaful/uracil, doxifluridine, tegaful/gimeracil/oteracil, capecitabine, cytarabine, enocitabine, gemcitabine, 6-mercaptopurine, fuludarabin, pentostatin, cladribine, hydroxyurea, doxorubicin, epirubicin, daunorubicin, idarubicine, pirarubicin, mitoxantrone, amurubicin, actinomycin D, bleomycine, pepleomycin, mytomycin C, aclarubicin, zinostatin, vincristine, vindesine, vinblastine, vinorelbine, paclitaxel, docetaxel, irinotecan, irinotecan active metabolite (SN-38), nogitecan (topotecan), etoposide, prednisolone, dexamethasone, tamoxifen, toremifene, medroxyprogesterone, anastrozole, exemestane, letrozole, rituximab, imatinib, gefitinib, gemtuzumab ozogamicin, bortezomib, erlotinib, cetuximab, bevacizumab, sunitinib, sorafenib, dasatinib, panitumumab, asparaginase, tretinoin, arsenic trioxide, salts thereof, or active metabolites thereof is exemplified. Of those, platinum-based complex anticancer agents and plant alkaloid-derived anticancer agents are preferred and oxaliplatin, cisplatin, irinotecan, SN-38, or a salt thereof is particularly preferred.

EXAMPLES

Next, the present invention is described in more detail by way of examples.

Example 1

(1) Method (a) Cells Used 11 kinds of human colorectal cancer cell lines (COLO201, COLO205, COLO320, DLD-1, HCT-15, HT-29, LS174T, SW480, SW620, SW1116, and WiDR) were obtained from the following (Table 1).

The culture was performed in a $\phi$100 mm/tissue culture dish (IWAKI) for adherent cells and a $\phi$100 mm/non-treated dish (IWAKI) for suspension cells by using a medium (RPMI 1640, 2 mM glutamine, 10% fetal bovine serum) at 37° C. under 5% $CO_2$.

TABLE 1

11 kinds of human colorectal cancer cell lines

| Name of cell line | Bank from which cell line is obtained | Deposition organization (or manufacturer) | Resource number or the like | Lot number or the like |
|---|---|---|---|---|
| COLO201 | JCRB | Health Science Research Resources Bank, Japan Health Sciences Foundation | JCRB0226 | 11252003 |
| COLO205 | TKG | Cell Resource Center for Biomedical Research, Institute of Development, Aging and Cancer, Tohoku University | TKG0457 | I-4439 |
| COLO320 | RCB | RIKEN BioResource Center | RCB1193 | 003 |
| DLD-1 | ECACC | (Dainippon Sumitomo Pharma Co., Ltd.) | EC-90102540 | 00/J/025 |
| HCT-15 | TKG | Cell Resource Center for Biomedical Research, Institute of Development, Aging and Cancer, Tohoku University | TKG0504 | I-4608 |
| HT-29 | ECACC | (Dainippon Sumitomo Pharma Co., Ltd.) | EC-91072201 | 04/I/004 |
| LS174T | TKG | Cell Resource Center for Biomedical Research, Institute of Development, Aging and Cancer, Tohoku University | TKG0406 | I-4468 |
| SW480 | ECACC | (Dainippon Sumitomo Pharma Co., Ltd.) | EC-87092801 | 02/A/030 |
| SW620 | ATCC | (Summit Pharmaceuticals International Corporation) | CCL-227 | 2324584 |
| SW1116 | ECACC | (Dainippon Sumitomo Pharma Co., Ltd.) | EC-87071006 | 02/A/063 |
| WiDR | ECACC | (Dainippon Sumitomo Pharma Co., Ltd.) | EC-85111501 | 00/H/001 |

(b) Drug

The bulk powder of oxaliplatin (L-OHP) was obtained from Yakult Honsha, Co., Ltd.

(c) Evaluation of Sensitivity to Oxaliplatin

After exposure of each cell line to 0 to 1,000 μmol/L oxaliplatin for 48 hours, a cell survival rate was evaluated with MTS assay (CellTiter96™ AQ$_{ueous}$ One Solution Cell Proliferation Assay, Promega). Then, $IC_{50}$ value (a concentration at which the number of cells is suppressed to 50% with respect to that in an oxaliplatin-untreated well) was calculated and used as an oxaliplatin sensitivity in each cell line. The evaluation of the sensitivity was performed four times with cells having different passage numbers and the average value and the standard deviation value thereof were calculated.

(d) Extraction of Intracellular Protein

A medium was removed from a dish, adherent cells were washed with ice-cold PBS three times and then collected by scraping with a rubber policeman. Suspension cells were washed three times by repeating centrifugation and suspension with PBS. The thus obtained each cell suspension was transferred to a 1.5-mL microtube; the cell suspension was centrifuged at 4° C. and 1,200×g for 10 minutes to collect the cells; after the supernatant was removed, 400 µL of a cell lysis buffer (9 mol/L Urea, 2% CHAPS, 1 mM DTT, protease inhibitor cocktail (Sigma)) were added thereto; the cells were subjected to ultrasonic treatment under ice cooling; the suspension was centrifuged at 4° C. and 16,000×g for 20 minutes; the supernatant was frozen rapidly with liquid nitrogen; and the frozen resultant was stored at −80° C. until the analysis. A part of the supernatant was used to perform protein quantification (DC Protein Assay Kit, Bio-Rad).

(e) Sample Preparation for Protein Expression Analysis with ProteinChip and Expression Analysis of Intracellular Protein A sample was adjusted to have a protein concentration of 5 mg/mL with a cell lysis buffer (excluding protease inhibitor) and then adjusted to have a concentration of 1 mg/mL with a dilution/wash buffer (50 mM sodium acetate buffer) (hereinafter, referred to as buffer) having a pH of 4.5. 100 µl of the adjusted sample were applied to each spot of a cation-exchange Proteinchip array (CM10, Bio-Rad) which had been pretreated with the same buffer, followed by reaction by incubation for 1 hour. After that, the spot was washed three times with the buffer and rinsed twice with milli-Q water. After drying by air, 0.5 µl of energy absorbing molecule (EAM: a saturated solution of sinapinic acid in 50% ACN/0.5% TFA solution) was applied to each spot twice separately. After the spot surface was dried, the analysis of the Protein-Chip array was performed.

The protein expression was analyzed with surface-enhanced laser desorption/ionization time-of-flight mass spectrometer (SELDI-TOF MS). As an analyzer, ProteinChip™ Reader (Model PBSIIC, Bio-Rad) was used. The analysis was performed under the following conditions: opitimization range of a mass-to-charge ratio (m/z), 2,000 to 30,000 daltons; laser intensity, 220; detector sensitivity, 8; and 104 shots in total per sample. The extraction of the peak having a signal-to-noise ratio (S/N ratio) of 5 or more and the protein expression comparison analysis were performed by using CiphergenExpress™ Data Manager 3.0.

(f) Correlation Analysis Between Protein Expression and Oxaliplatin Sensitivity

The relation between an $IC_{50}$ value and a peak intensity of each cell line was analyzed for all protein peaks detected by SELDI-TOF MS. The linear regression analysis was performed about the relationship between a logarithm value of the $IC_{50}$ value and the peak intensity. A protein having a peak which satisfies the following relationships was selected as an oxaliplatin sensitivity-related candidate protein: P value<0.05; and determination coefficient ($r^2$; r, Pearson correlation coefficient)>0.5. The correlation analysis and the linear regression analysis were performed by using SPSS15.0J for Windows (registered trade mark) (version 15.0.1).

(2) Results (a) Evaluation of Oxaliplatin Sensitivity in 11 Kinds of Human Colorectal Cancer Cell Lines The $IC_{50}$ value of each cell line was 0.84±0.20 to 29.7±13.6 µM and there was recognized a wide range in the sensitivity (FIG. 1).

(b) Protein Expression Analysis 42 peaks in total were detected by the expression analysis using SELDI-TOF MS under the above-mentioned analysis conditions.

(c) Correlation Analysis Between Protein Expression and Oxaliplatin Sensitivity

Figure 2:
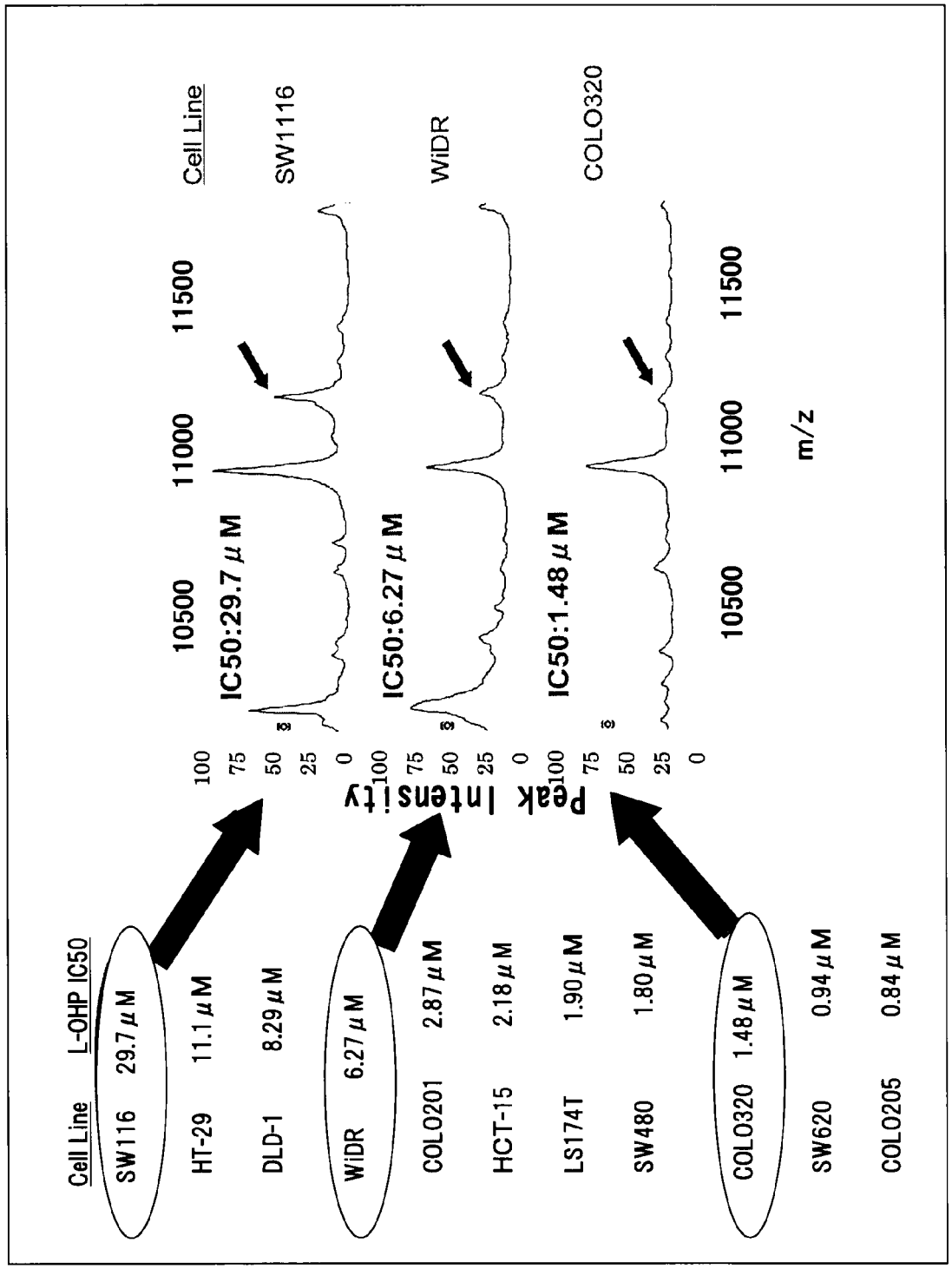
FIG. 2 is a graph illustrating sensitivity to oxaliplatin (L-OHP) and change in a peak intensity of protein A1 in each cancer cell line.
Figure 3:
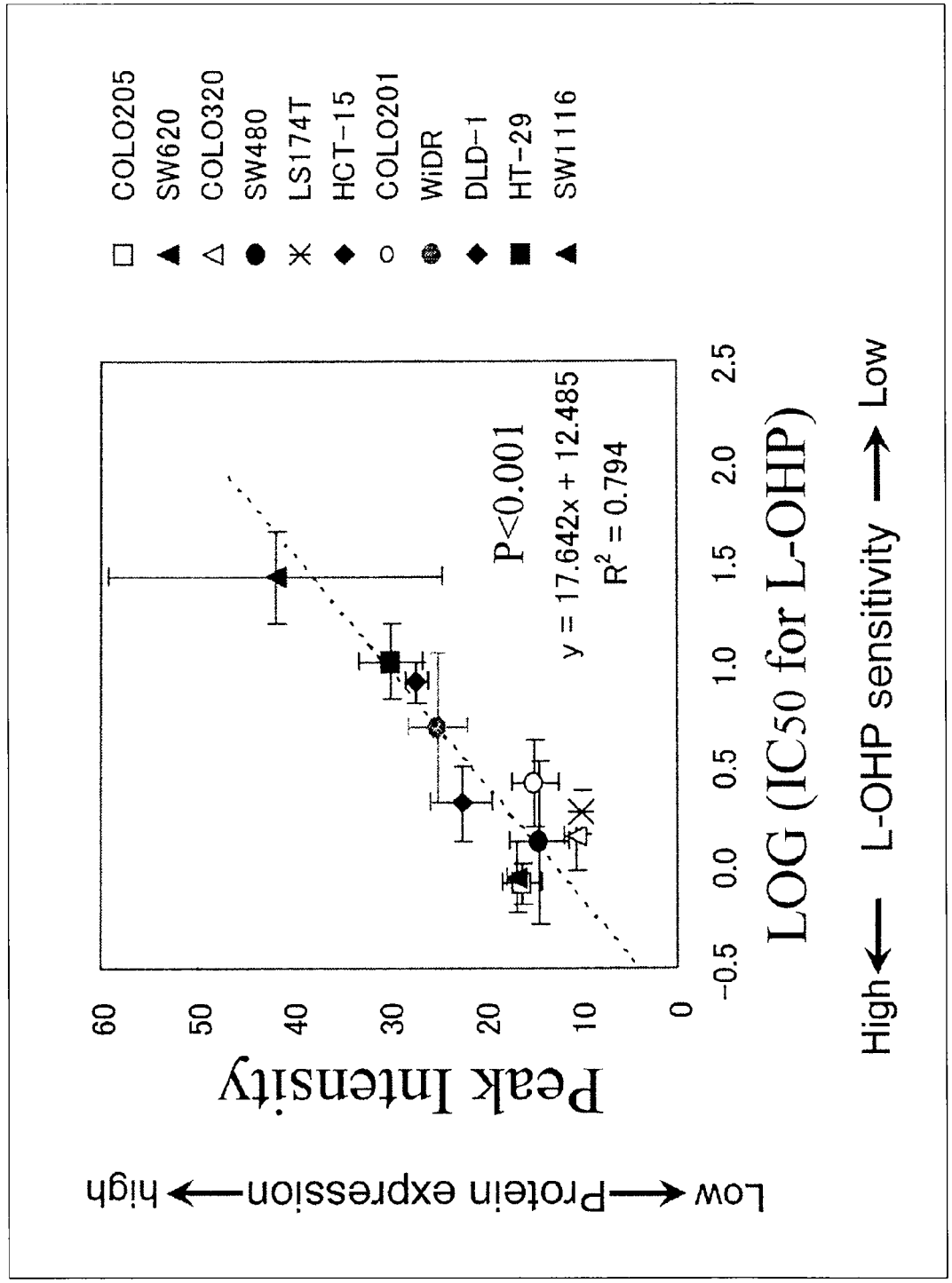
FIG. 3 is a diagram illustrating a correlation between the peak intensity of the protein A1 and the sensitivity to oxaliplatin (L-OHP) in each cancer cell line.

Through the correlation analysis and the linear regression analysis, the peak detected at m/z of 11,000 to 11,100 was found to have a significant correlation with the oxaliplatin sensitivity ($IC_{50}$ value) (FIG. 2 and FIG. 3).

Example 2

(1) Method

As cells, 7 kinds of human colon cancer cell lines (DLD-1, HCT-15, HT-29, LS174T, SW480, SW620, and WiDR), and as a drug, cisplatin (cis-Diammineplatinum(II) dichrolide, SIGMA) were used. The cell survival rate after exposure to 0 to 1,000 µmol/L cisplatin for 48 hours was evaluated by MTS assay in the same manner as in Example 1 and the $IC_{50}$ value was calculated. The extraction of the intracellular protein, the protein expression analysis, and the correlation analysis between the protein expression and the cisplatin (CDDP) sensitivity were performed in the same way as in Example 1.

(2) Results (a) Evaluation of Cisplatin Sensitivity in 7 Kinds of Human Colorectal Cancer Cell Lines The $IC_{50}$ value of each cell line was 3.33±0.80 to 26.9±11.6 µM and there was recognized a wide range in the sensitivity.

(b) Correlation Analysis Between Protein Expression and Cisplatin Sensitivity

Figure 4:
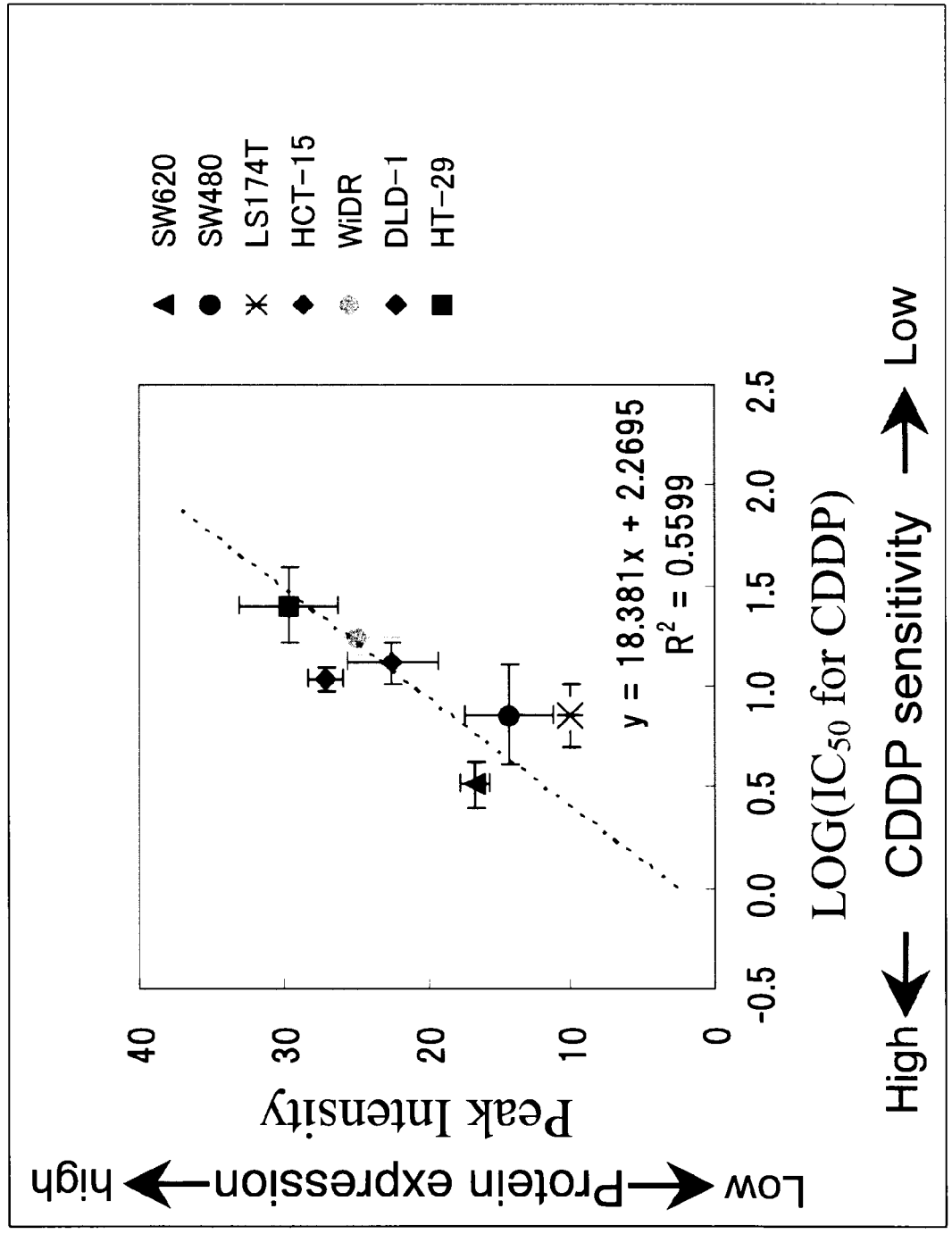
FIG. 4 is a diagram illustrating a correlation between the peak intensity of the protein A1 and sensitivity to cisplatin (CDDP) in each cancer cell line.
Figure 5:
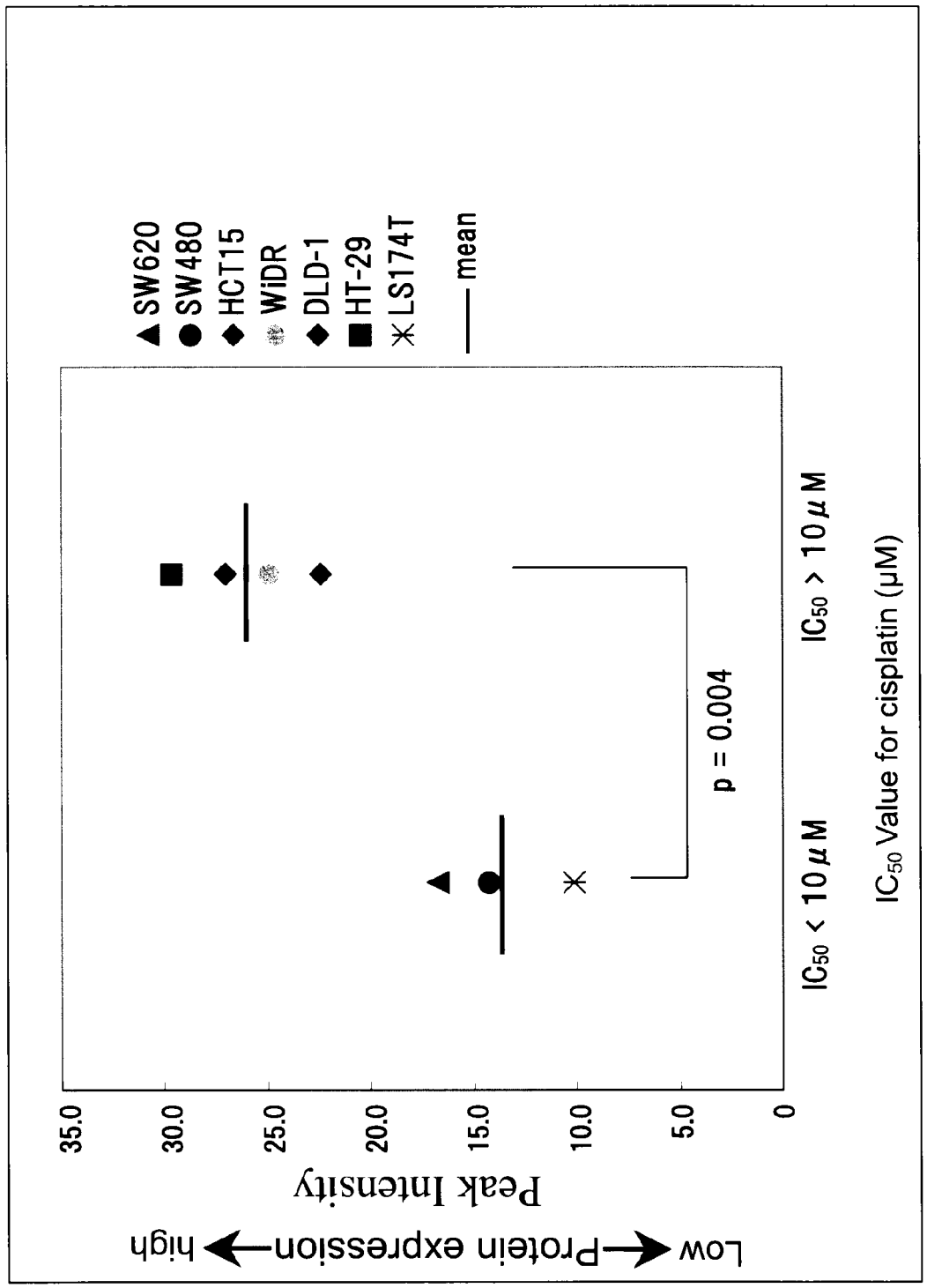
FIG. 5 is a diagram illustrating a relationship between the peak intensity of the protein A1 and the sensitivity to cisplatin (CDDP) in each cancer cell line (cell lines are classified into two groups and compared by setting a cut off value of $IC_{50}$ with respect to cisplatin to 10 μM).

Through the correlation analysis and the linear regression analysis, the peak detected at m/z of 11,000 to 11,100 was recognized to show tendency of a correlation with cisplatin sensitivity ($IC_{50}$ value) (FIG. 4). Further, based on the pharmacokinetic parameters of total platinum at the time of the administration of the cisplatin (Briplatin™ injection, interview form), when a maximum dose (100 mg/m$^2$) for once in a clinical use of cisplatin was administered, a peak concentration in blood ($C_{max}$) thereof was calculated to be about 9.5 to 11.0 µM (calculated when the body surface area of Japanese was set to 1.50 to 1.73 m$^2$). Therefore, a cutoff value was set to 10 µM for the $IC_{50}$ value of each cancer cell line with respect to cisplatin and the cancer cell lines were classified into two groups of a high sensitivity group and a low sensitivity group. As a result, there was a significant increase in the peak intensity of the peak detected at m/z of 11,000 to 11,100 in the low sensitivity group (FIG. 5).

Example 3

(1) Method

As cells, 5 kinds of human colorectal cancer cell lines (COLO320, HCT-15, HT-29, LS174T, HCT116 (HCT116 was obtained from ECACC)), and as a drug, an irinotecan active metabolite (SN-38, obtained from Yakult Honsha, Co., Ltd.) were used. The cell survival rate after exposure to 0 to 1,000 nmol/L SN-38 for 72 hours was evaluated by MTS assay in the same manner as in Example 1 and the $IC_{50}$ value was calculated. The extraction of the intracellular protein and the sample preparation for ProteinChip analysis were performed in the same way as in Example 1. For the analysis, ProteinChip™ Reader (Model PCS4000 Personal Edition, Bio-Rad) was used, and the analysis was performed under the following conditions: mass range, 0 to 70,000 daltons; focus mass, 11,000 daltons; energy, 3,000 nJ; and 265 shots in total per sample. The protein expression analysis was performed by using CiphergenExpress™ Data Manager 3.0.

(2) Results (a) Evaluation of SN-38 Sensitivity in 5 Kinds of Human Colorectal Cancer Cell Lines The $IC_{50}$ value of each cell line was 3.39 to 33.7 nM and there was recognized a wide range in the sensitivity.

(b) Correlation Analysis Between Protein Expression and SN-38 Sensitivity

Figure 6:
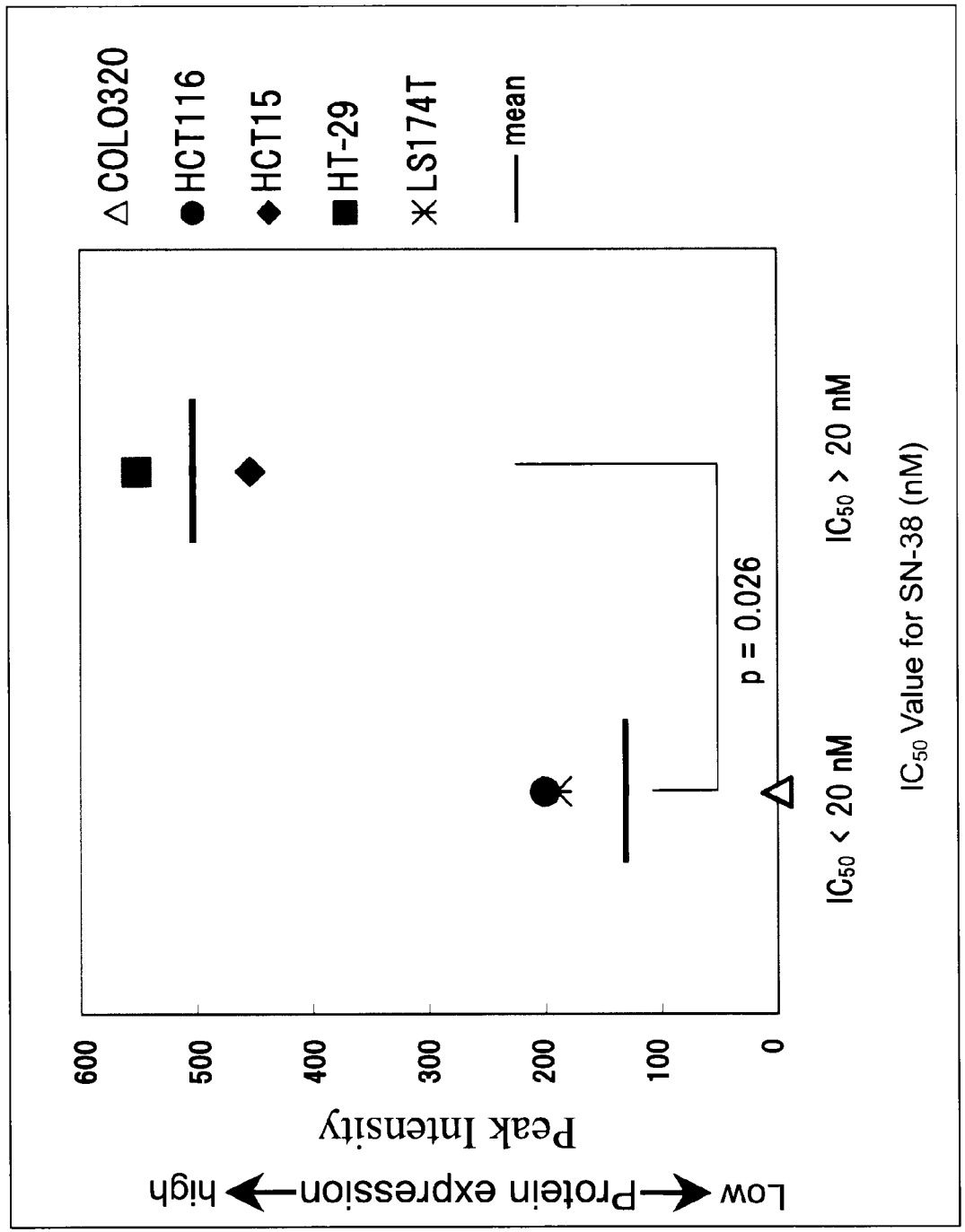
FIG. 6 is a diagram illustrating a relationship between the peak intensity of the protein A1 and sensitivity to SN-38 in each cancer cell line (cell lines are classified into two groups and compared by setting a cut off value of $IC_{50}$ with respect to SN-38 to 20 nM).

Based on the pharmacokinetic parameters of SN-38 (Campto™, interview form), the area under the curve of SN-38 blood concentration ($AUC_{SN-38}$) obtained after the first irinotecan administration of the colon cancer therapy regimen (180 mg/m²/day) was calculated to be 1,449 nmol·h/L. The concentration of SN38 required to obtain the same exposure amount through 72-hour exposure employed in this Example was calculated to be 20 nM. Therefore, a cut off value was set to 20 nM for the $IC_{50}$ value of each cancer cell line with respect to SN-38 and the cancer cell lines were classified into two groups of a high sensitivity group and a low sensitivity group. As a result, there was a significant increase in the peak intensity of the peak detected at m/z of 11,000 to 11,100 in the low sensitivity group (FIG. 6).

Example 4

In order to study the property of the protein detected as a peak at m/z of 11,000 to 11,100 (protein A1) in Example 1, there were examined change in the peak intensity associated with change in pH, and whether the protein A1 could be detected or not in a ProteinChip array whose chip surface was subjected to a chemical modification different from that of a CM10 chip array.

(1) Method (a) Proteinchip Array and Buffer Conditions Used for Examination

For the cation-exchange ProteinChip array (CM10, Bio-Rad) and the anion-exchange ProteinChip array (Q10, Bio-Rad), the following 15 kinds of buffers were used: pH3.0 (50 mM glycine-HCl buffer); pH 3.5 (50 mM sodium acetate buffer); pH 4.0 (50 mM sodium acetate buffer); pH 4.5 (50 mM sodium acetate buffer); pH 5.0 (50 mM sodium acetate buffer); pH 5.5 (50 mM sodium acetate buffer); pH 6.0 (50 mM phosphate buffer); pH 6.5 (50 mM phosphate buffer); pH 7.0 (50 mM phosphate buffer); pH 7.5 (50 mM phosphate buffer); pH 8.0 (50 mM Tris-HCl buffer); pH 8.5 (50 mM Tris-HCl buffer); pH 9.0 (50 mM glycine-NaOH buffer); pH 9.5 (50 mM glycine-NaOH buffer); and pH 10.0 (50 mM glycine-NaOH buffer). For the immobilized metal affinity capture ProteinChip array (IMAC30, Bio-Rad), phosphate buffered saline (PBS) was used.

(b) Sample Preparation for Analysis Using CM10 and Q10 Arrays and Analysis Condition The sample preparation for analysis using CM10 or Q10 arrays and production of protein chip arrays were conducted using each buffer in the item (a) and according to the item (e) of the section "(1) Method" in Example 1. Note that, as an analyzer, ProteinChip™ Reader (Model PCS4000 Personal Edition, Bio-Rad) was used, and the analysis was performed under the following conditions: mass range, 0 to 70,000 daltons; focus mass, 11,000 daltons; energy, 3,000 nJ; and 265 shots in total per sample.

(c) Sample Preparation for Analysis Using IMAC30 Array and Analysis Condition

The spot surface of IMAC30 array was activated with 50 mM $NiSO_4$ and rinsed once with milli-Q water. Then, the spots were pretreated with PBS. The sample preparation, and application of the sample to the chip surface and subsequent procedures were conducted using PBS described in the item (a) as a buffer and according to the item (e) of the section "(1) Method" in Example 1. Note that, as an analyzer, ProteinChip™ Reader (Model PCS4000 Personal Edition, Bio-Rad) was used, and the analysis was performed under the following conditions: mass range, 0 to 70,000 daltons; focus mass, 11,000 daltons; energy, 6,000 nJ; and 265 shots in total per sample.

(2) Results

It was recognized that the peak of the candidate protein detected as a peak at m/z of 11,000 to 11,100 in Example 1 in such analysis conditions that CM10 array was used and pH was 4.5 was remarkably lowered at pH of 7.0 to 7.5 in both CM10 array and Q10 array. The isoelectric point (pI) of the candidate protein was estimated to be 7.0 to 7.5. In addition, the candidate protein was also detected in IMAC30 chip array whose chip surface was activated with $NiSO_4$.

Example 5

Identification of Candidate Protein A1

(1) Estimation of Molecular Weight of Candidate Protein A1

Figure 7:
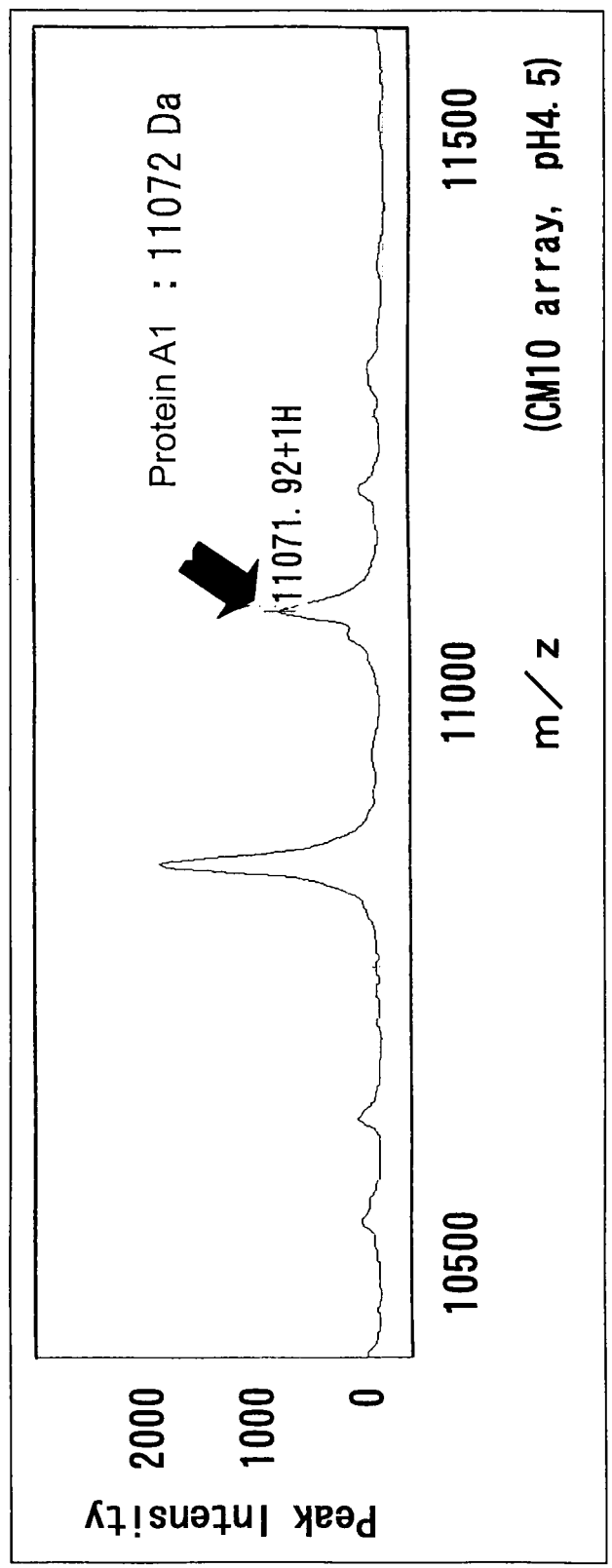
FIG. 7 is a diagram illustrating a molecular weight of the protein A1 by an SELDI-TOF MS analysis using a protein chip array.

By using, as calibrants, bovine insulin (5,733.51 Da) and equine cytochrome c (12,360.96 Da) whose molecular weights have been known, the intracellular protein extraction sample was subjected to internal calibration by using SELDI-TOF MS in the same analysis conditions (CM10 array and 50 mM sodium acetate buffer, pH 4.5) as in the protein expression analysis. As a result, the molecular weight of the candidate protein A1 peak was estimated to be 11,072 Da (FIG. 7).

(2) Purification and Identification of Candidate Protein A1 (Purification)

In order to purify and identify the candidate protein A1, the intracellular proteins were extracted from two cell lines, the cell line HT-29 expressing a high level of the candidate protein and the cell line COLO320 expressing a low level of the candidate protein, by the same method as in the expression analysis. Both samples in an equal amount were taken based on the result of the protein quantification, and precipitated with TCA. After that, the collected precipitates were washed with an ice ethanol/ether solvent and dried at room temperature. IEF lysis buffer (6 M urea, 2 M thiourea, 3% CHAPS, 1% Triton X-100, DeStreak reagent, GE Healthcare) was added to the precipitates and the resultant was stirred at room temperature, followed by ultrasonic treatment.

The prepared IEF sample solution was centrifuged and the supernatant was applied to an immobiline drystrip gel (pH 3 to 10, non-linear, 13 cm, GE Healthcare). The gel was swelled, and thereafter, isoelectric focusing was performed (5,000 V, 15 hr).

After the completion of isoelectric focusing, the immobiline drystrip gel was equilibrated in a sample buffer for two-dimensional electrophoresis (6 M urea, 20% glycerol, 2% DTT, 2% SDS, 100 mM Tris-HCl pH 8.8). The equilibrated immobiline drystrip gel was subjected to electrophoresis at a constant current of 25 mA. As the gel, used was a polyacrylamide gradient gel (10 to 18% gradient, 16×16 cm (BIO CRAFT)). The gel after electrophoresis was stained with CBB G-250 and decolorized with 5% acetic acid.

The image of two-dimensional electrophoresis was obtained with GS-800 calibrated imaging densitometer (Bio-Rad) and the image was analyzed with PDQuest software (Bio-Rad). Then, an analysis for comparison was performed.

(Identification)

Figure 8:
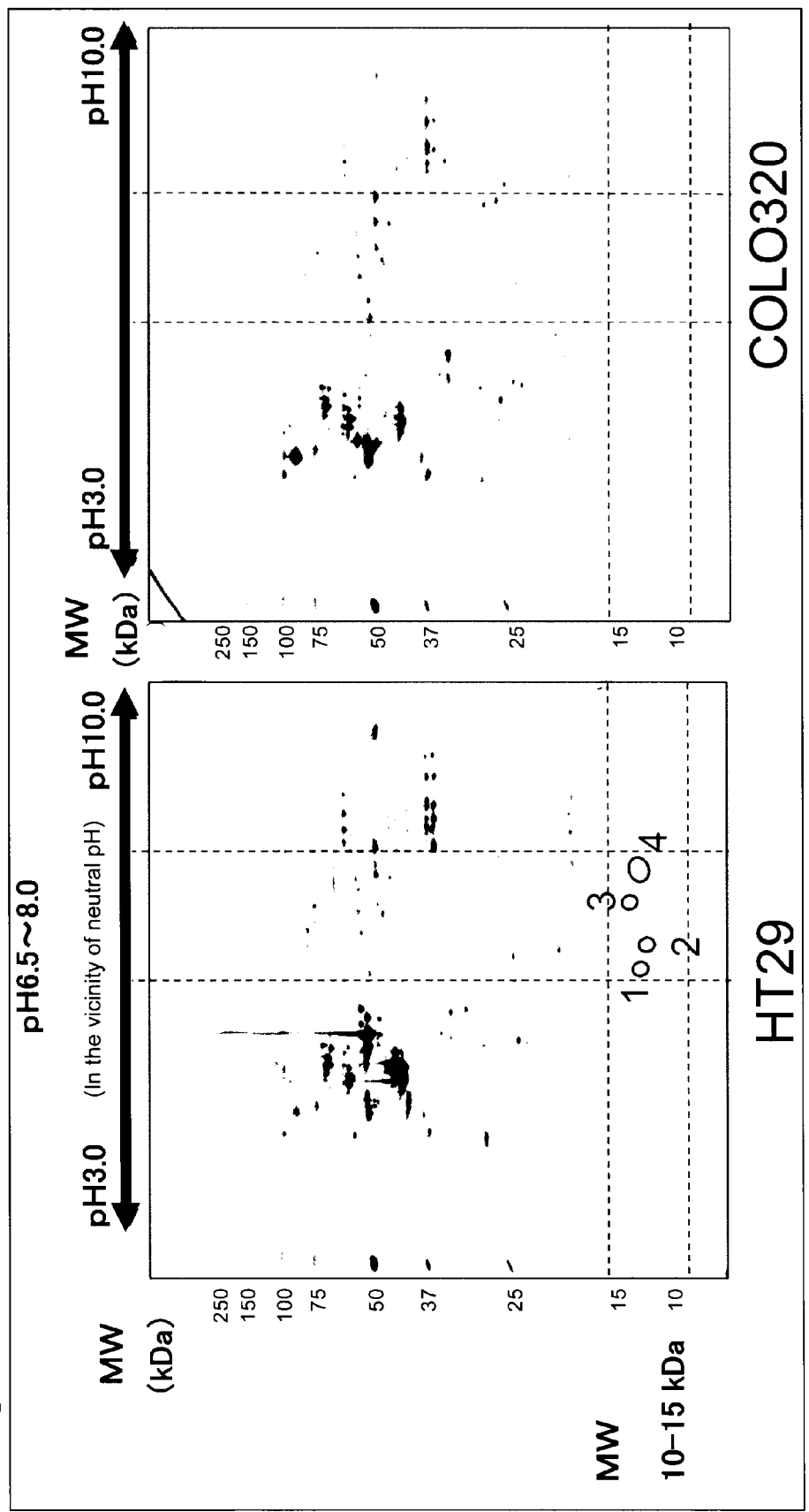
FIG. 8 illustrates developments of two-dimensional electrophoresis of two kinds of colorectal cancer cell lines HT-29 (expressing the protein A1 at a high level) and COLO320 (expressing the protein A1 at a low level) and selected spots for an LC/MS/MS analysis.

Based on the information about the candidate protein A1 (molecular weight: 11,072, pI: 7.0 to 7.5) obtained by the SELDI-TOF MS analysis using the ProteinChip, targeted were spots present on the gel developed by two-dimensional electrophoresis and in the following range: molecular weight, 10 to 15 kDa; and pI, about 6.5 to 8.0 (in the vicinity of the neutral pH). Of those spots, 4 spots showing high expression level in HT-29 compared with COLO320 were selected (FIG. 8). Those spots were cut off, and the proteins were digested with trypsin in the gel according to a known method. After that, the proteins were analyzed (MS/MS measurement) using liquid chromatography/mass spectrometry ion trap time-of-flight (LCMS-IT-TOF, Shimadzu), and the obtained results were subjected to MASCOT database search.

Of the analyzed 4 spots, the protein A1 (molecular weight: 11,072, pI: 7.3) identified with the spot 4 illustrated in FIG. 8 corresponded to the result obtained by the SELDI-TOF MS analysis (molecular weight: 11,072, pI: 7.0 to 7.5). From the foregoing, the candidate protein A1 which showed a correlation with oxaliplatin sensitivity and was detected as a peak showing m/z of 11,000 to 11,100 was identified as S100A10 (S100 calcium-binding protein A10, Calpactin-1 light chain, Calpactin I light chain, p10 protein, p11, Cellular ligand of annexin II).

Example 6

S100A7 and S100A8

The intracellular protein extraction sample from a cancer cell line was analyzed using a CM10 array and 50 mM Tris-HCl buffer (pH 8.0) in the same conditions as those in the item (e) of the section "(1) Method" in Example 1. As a result, two protein peaks related with the oxaliplatin sensitivity, i.e. peaks of protein A2 and protein A3, were found.

Figure 9:
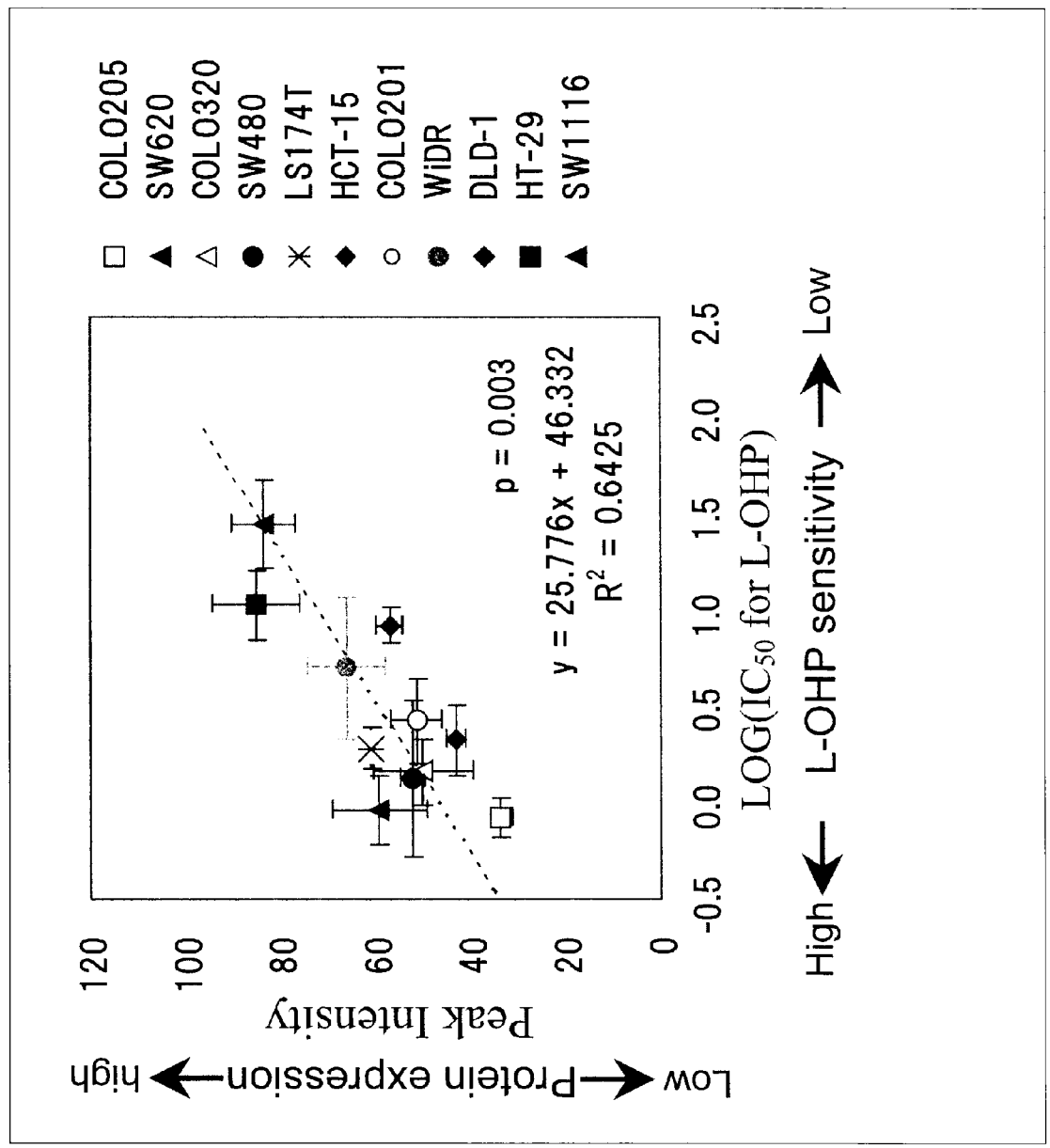
FIG. 9 is a diagram illustrating a correlation between a peak intensity of protein A2 and sensitivity to oxaliplatin in each cancer cell line.

The peak intensity of the protein A2 showed a significant correlation with the oxaliplatin (L-OHP) sensitivity ($IC_{50}$ value) of each cancer cell line (FIG. 9).

Figure 10:
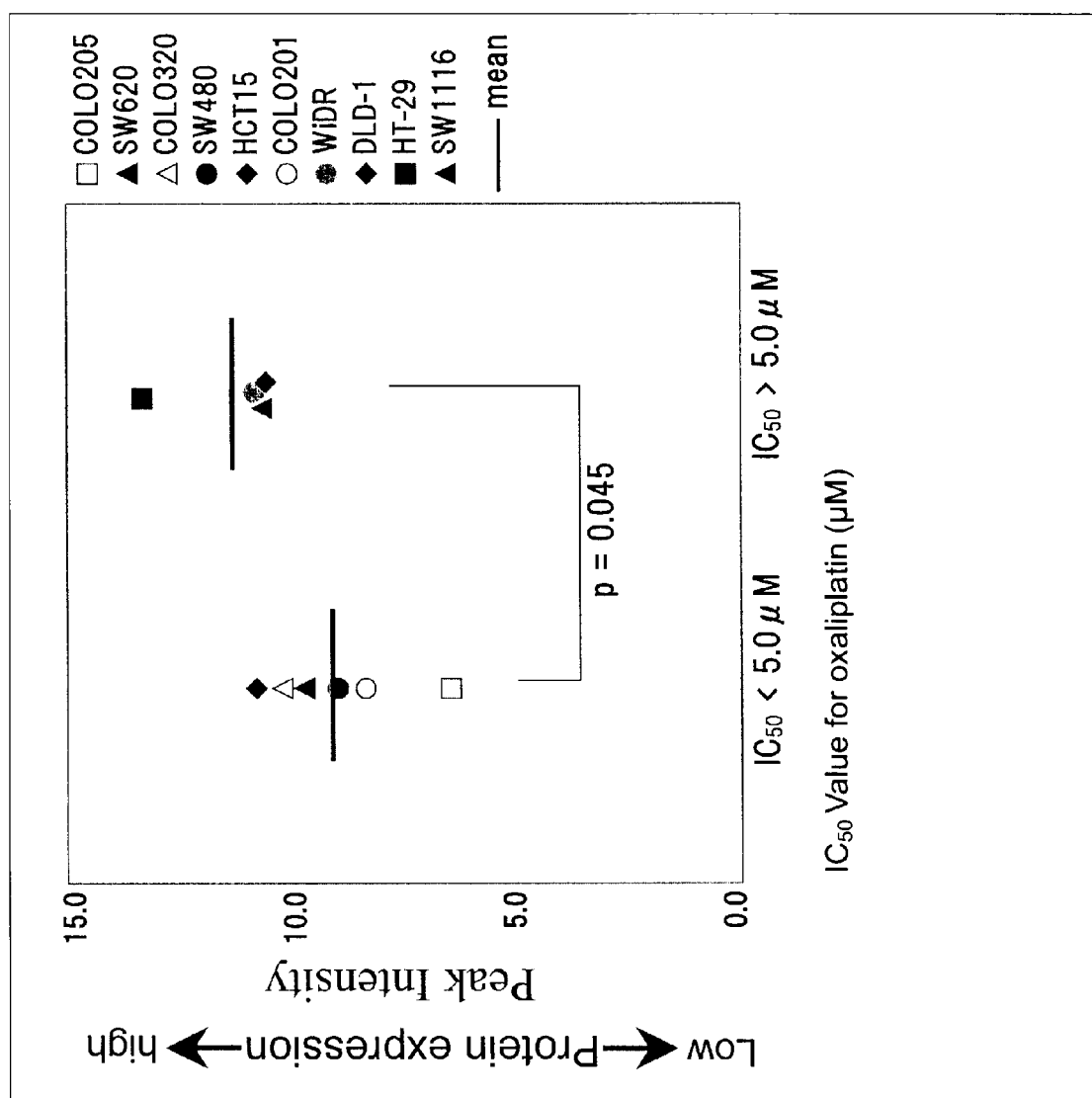
FIG. 10 is a diagram illustrating a relationship between a peak intensity of protein A3 and sensitivity to oxaliplatin in each cancer cell line (cell lines are classified into two groups and compared by setting a cut off value of $IC_{50}$ with respect to oxaliplatin to 5.0 μM).

In addition, based on the $IC_{50}$ value of each cell line with respect to the oxaliplatin, the cancer cell lines were classified into two groups of a high sensitivity group and a low sensitivity group with a cut off value of 5.0 μM which was roughly corresponding to a peak blood concentration at the time of clinical use of the oxaliplatin. As a result, there was a significant increase in the peak intensity of the protein A3 in the low sensitivity group (FIG. 10). Note that, the cell line LS174T was excluded from the targets of the analysis because the S/N ratio was less than 5.

The peaks of the protein A2 and protein A3 were present in the vicinity of the peak of S100A10. The calibration was performed by using bovine insulin (5,733.51 Da) and equine cytochrome c (12,360.96 Da) as calibrants. As a result, the protein A2 was supposed to have a molecular weight of 10,835 Da and the protein A3 was supposed to have a molecular weight of 11,340 Da.

As in Example 2, by using each of 15 kinds of buffers having a pH of 3.0 to 10.0 and each of a CM10 array and a Q10 array, change in each peak intensity was analyzed by SELDI-TOF MS. As a result, the peak with the molecular weight of 10,835 Da decreased remarkably at a pH of 6.5 to 7.0 and the peak with the molecular weight of 11,340 Da increased remarkably at a pH of 6.0 to 6.5, whereby pI was estimated to 6.5 to 7.0 and 6.0 to 6.5, respectively.

Figure 11:
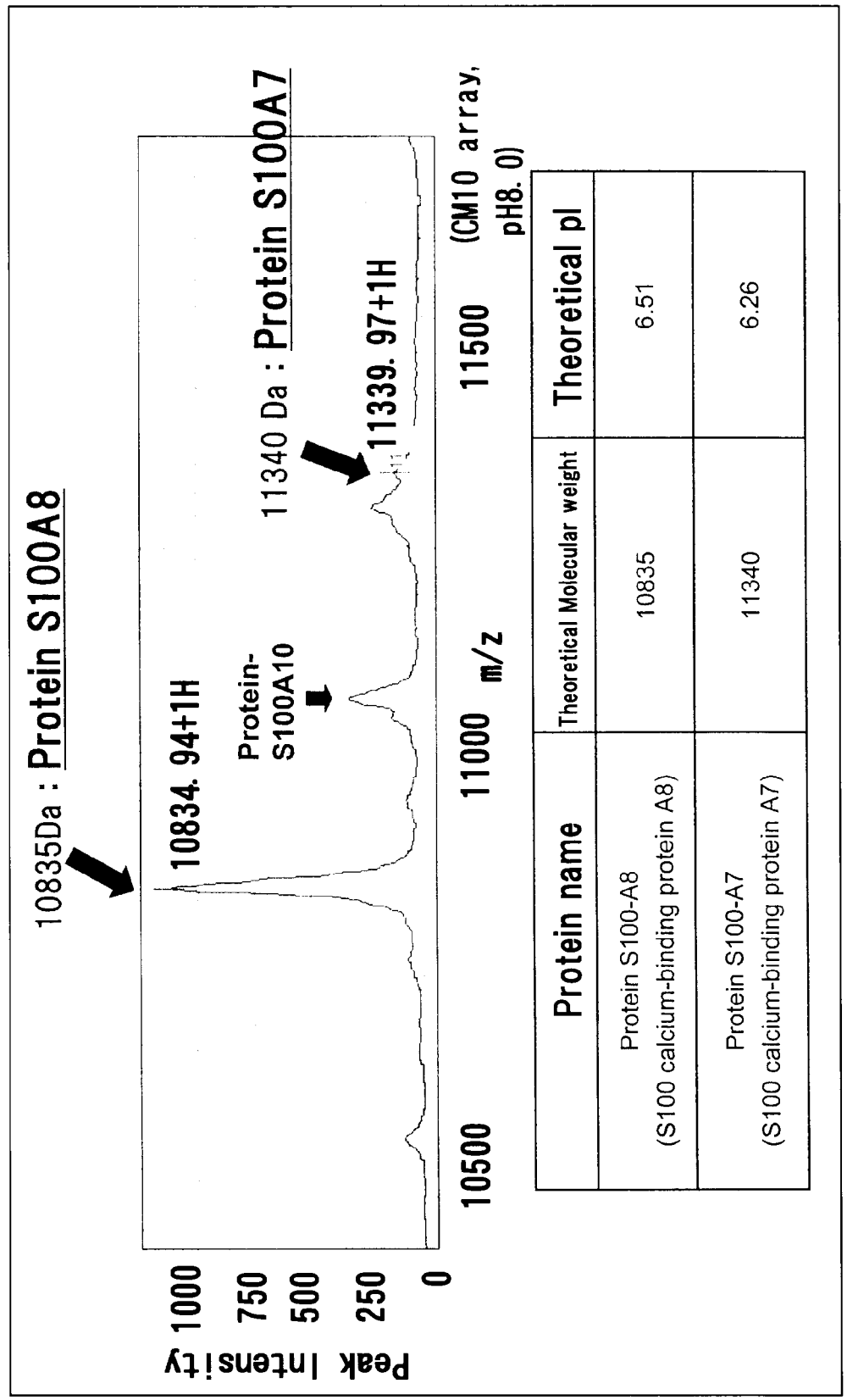
FIG. 11 illustrates protein A2 (protein S100-A8, S100 calcium-binding protein A8) and protein A3 (protein S100-A7, S100 calcium-binding protein A7) by an SELDI-TOF MS analysis using a protein chip array.

Based on those results, the proteins were searched in a database (Expasy TagIdent tool. As a result, the peak showing 10,835 Da was found to be S100A8 (S100 calcium-binding protein A8, Calgranulin-A, Migration inhibitory factor-related protein 8, MRP-8, p8, or the like) and the peak showing 11,340 Da was found to be S100A7 (S100 calcium-binding protein A7, Psoriasin) (FIG. 11).

Comparative Example 1

Figure 12:
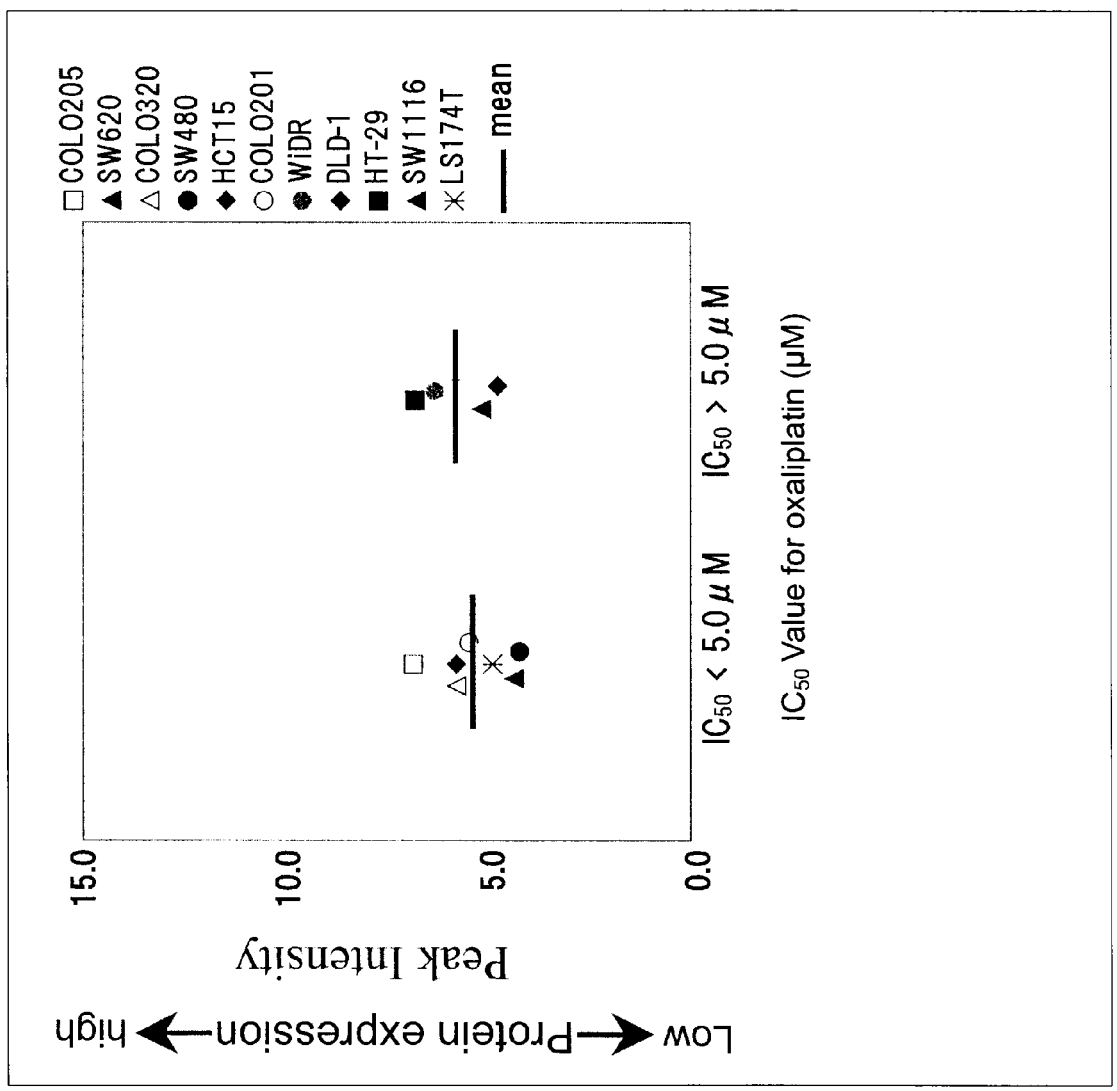
FIG. 12 is a diagram illustrating a relationship between a peak intensity of S100A9 and sensitivity to oxaliplatin in each cancer cell line (cell lines are classified into two groups and compared by setting a cut off value of $IC_{50}$ with respect to oxaliplatin to 5.0 μM).

As in Example 6, the peak estimated to be S100A9 having a molecular weight of 13,242 by SELDI-TOF MS was studied on the relationship with the oxaliplatin sensitivity. As a result, there was no significant relationship between the expression level of S1009A and the oxaliplatin sensitivity (FIG. 12). Accordingly, it was revealed that there is no relationship between S100A9 and the anticancer agent sensitivity.

Example 7

(1) Method

From HT-29 cells expressing a high level of the peak detected at m/z of 11,000 to 11,100 and COLO320 cells expressing a low level of the peak, intracellular proteins were extracted by the same method as in Example 1. 10 μg of the proteins were applied in each lane of 16.5% polyacrylamide gel and SDS-PAGE was performed at a constant voltage of 100 V. After electrophoresis, the proteins were blotted on a PVDF membrane by using a dry blotting system (iBlot™, Invitrogen). After blocking was conducted, S100A10 and an endogenous protein were reacted with primary antibodies, i.e. anti-S100A10 monoclonal antibody (purified mouse anti-annexin II light chain monoclonal antibody, BD Transduction Laboratories) and anti-GAPDH monoclonal antibody (Ambion), respectively, followed by the reaction with a secondary antibody of an alkali phosphatase-labeled anti-mouse IgG antibody. Then, a CDP-Star™ chemiluminescent substrate as a reaction substrate was added and luminescence was detected by Luminoimage analyzer (LAS-4000mini, FUJIFILM). As a blocking reagent, a secondary antibody, and a reaction substrate, those included in Chemiluminescent Western Blot Immunodetection Kit (WesternBreeze™, Invitrogen) were used.

(2) Result

Figure 13:
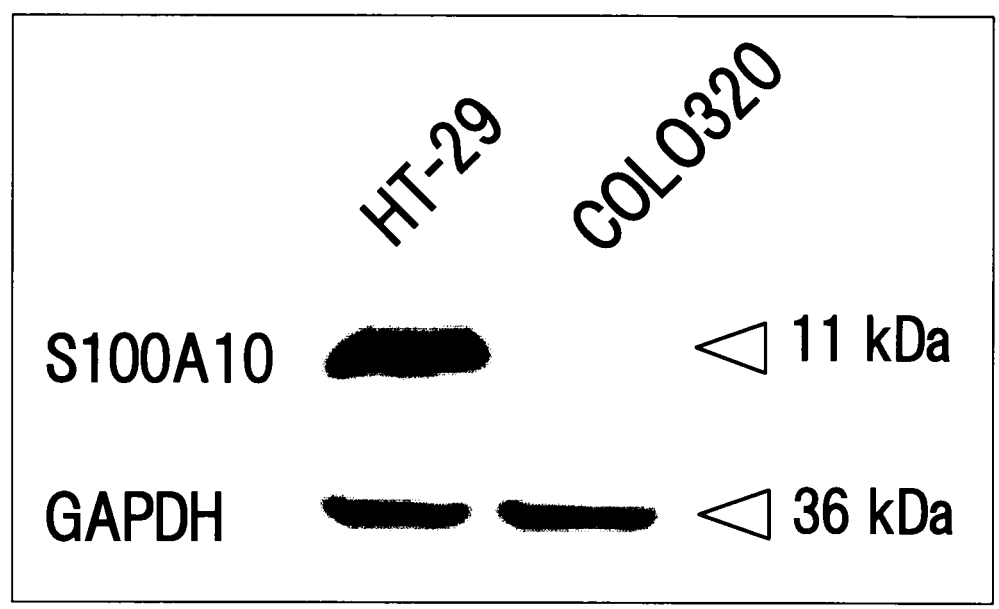
FIG. 13 is a drawing illustrating detection of S100A10 in HT-29 (expressing S100A10 at a high level) and COLO320 (expressing S100A10 at a low level) by western blotting.

The expressions of S100A10 in HT-29 cells expressing a high level of the peak, which was detected at m/z of 11,000 to 11,100 in the protein expression analysis using a ProteinChip array (Example 1), and in COLO320 cells expressing a low level of the peak were confirmed by western blotting using the anti-S100A10 monoclonal antibody (FIG. 13).

The invention claimed is:
1. A method of treating colorectal cancer, comprising:
  (1) measuring a concentration of at least one calcium-binding protein selected from the group consisting of S100A7, S100A8, and S100A10 in a biological specimen from a subject with colorectal cancer; and
  (2) administering at least one anticancer agent selected from the group consisting of oxaliplatin, cisplatin, irinotecan, SN-38, and a salt thereof to the subject when the concentration of the calcium-binding protein is lower than a predetermined standard concentration for the anticancer agent, or when the concentration of the calcium binding protein does not reach a predetermined standard concentration which is set for the anticancer agent during the administration of the anticancer agent, excluding the combination of S100A10 and cisplatin.

2. The method of claim 1, which comprises
(2) administering at least one anticancer agent selected from the group consisting of oxaliplatin, cisplatin, irinotecan, SN-38, and a salt thereof to the subject when the concentration of the calcium-binding protein is lower than a predetermined standard concentration for the anticancer agent.

3. The method of claim 1, wherein the calcium-binding protein is S100A7.

4. The method of claim 1, wherein the calcium-binding protein is S100A8.

5. The method of claim 1, wherein the calcium-binding protein is S100A10.

6. The method of claim 1, wherein the anticancer agent is oxaliplatin or a salt thereof.

7. The method of claim 1, wherein the anticancer agent is cisplatin or a salt thereof.

8. The method of claim 1, wherein the anticancer agent is irinotecan or a salt thereof.

9. The method of claim 1, wherein the anticancer agent is SN-38 or a salt thereof.

10. The method of claim 1, wherein the subject has received the anticancer agent.

11. The method of claim 1, wherein the biological specimen is blood, plasma, a biopsy specimen of a cancer tissue, a preparation obtained by cancer extirpation, stool, urine, ascitic fluid, pleural fluid, cerebrospinal fluid, or expectoration.

12. The method of claim 1, wherein the biological specimen is serum.

13. The method of claim 1, wherein the concentration of the calcium-binding protein is measured by mass spectrometry.

14. The method of claim 1, wherein the concentration of the calcium-binding protein is measured with an antibody to the marker.

15. The method of claim 1, wherein the concentration of the calcium-binding protein is measured by radioimmunoassay, an enzyme immunoassay, a fluorescent immunoassay, a luminescence immunoassay, immunoprecipitation, immunonephelometry, immunostaining, or immunodiffusion.

16. The method of claim 1, wherein the concentration of the calcium-binding protein is measured by western blotting.

17. The method of claim 1, wherein the concentration of the calcium-binding protein is measured by enzyme-linked immunosorbent assay.

* * * * *